(12) United States Patent
Wu et al.

(10) Patent No.: US 12,004,719 B2
(45) Date of Patent: Jun. 11, 2024

(54) IMAGE SENSOR PACKAGE AND ENDOSCOPE

(71) Applicant: Medimaging Integrated Solution, Inc., Hsinchu (TW)

(72) Inventors: Shangyi Wu, Hsinchu (TW); Chu-Ming Cheng, Hsinchu (TW)

(73) Assignee: MEDIMAGING INTEGRATED SOLUTION, INC., Hsinchu (TW)

( * ) Notice: Subject to any disclaimer, the term of this patent is extended or adjusted under 35 U.S.C. 154(b) by 372 days.

(21) Appl. No.: 17/535,867

(22) Filed: Nov. 26, 2021

(65) Prior Publication Data
US 2022/0265130 A1 Aug. 25, 2022

(30) Foreign Application Priority Data

Feb. 19, 2021 (TW) .................................. 110105871
Jul. 29, 2021 (TW) .................................. 110127986

(51) Int. Cl.
| | |
|---|---|
| *H04N 5/335* | (2011.01) |
| *A61B 1/05* | (2006.01) |
| *G02B 23/24* | (2006.01) |
| *H01L 27/146* | (2006.01) |

(52) U.S. Cl.
CPC ............ *A61B 1/05* (2013.01); *G02B 23/2415* (2013.01); *G02B 23/2484* (2013.01); *H01L 27/14636* (2013.01)

(58) Field of Classification Search
CPC ....................... G02B 23/2484; G02B 23/2415
See application file for complete search history.

(56) References Cited

U.S. PATENT DOCUMENTS

| | | | |
|---|---|---|---|
| 11,309,299 B2* | 4/2022 | Wu ........................ | H05K 1/189 |
| 11,405,569 B2* | 8/2022 | Takahashi ......... | H01L 27/14621 |
| 11,558,534 B2* | 1/2023 | Numasawa ............... | A61B 1/05 |
| 2022/0265122 A1* | 8/2022 | Cheng .................... | A61B 1/051 |

* cited by examiner

*Primary Examiner* — Gary C Vieaux
(74) *Attorney, Agent, or Firm* — Muncy, Geissler, Olds & Lowe, P.C.

(57) ABSTRACT

An image sensor package includes a first substrate, an image sensor, a second substrate, a light-emitting element, and a first encapsulant. The image sensor is disposed on and electrically connected with the first substrate. The second substrate is disposed on and electrically connected with the first substrate, wherein the second substrate includes an accommodating portion and the image sensor protrudes from the second substrate via the accommodating portion. The light-emitting element is disposed on the second substrate and close to the image sensor, and is electrically connected to the second substrate. The first encapsulant is filled in a space between the image sensor and the light-emitting element. The abovementioned image sensor package can achieve miniaturization and provide better illumination. An endoscope including the abovementioned image sensor package is also disclosed.

40 Claims, 7 Drawing Sheets

IMAGE SENSOR PACKAGE AND ENDOSCOPE

BACKGROUND OF THE INVENTION

1. Field of the Invention

The present invention relates to an image sensor package and an endoscope, particularly to an image sensor package including an illumination element and an endoscope using the same.

2. Description of the Prior Art

An endoscope can reach cavities, which the naked eyes are unlikely to observe directly. Therefore, endoscopes have been extensively used in industry and medicine. Especially, the application of endoscopes to medicine favors medical diagnosis very much. An endoscope may access cavities of a human body through tiny channels of the human body. For an example, an endoscope may reach the lung through a bronchial tube. For another example, an endoscope may enter the bladder through the urinary tract. Hence, miniaturizing an endoscope has become an important subject of the concerned field.

Refer to FIG. 1. In a conventional endoscope 10, an image sensor 11 and light-emitting elements 12 are disposed on a flexible circuit board 13; cables 14 are soldered to the corresponding electric-conduction contacts 131 of the flexible circuit board 13. After the flexible circuit board 13 is bent to have the desired shape, the abovementioned elements are encapsulated with a plastic material to assume a fixed form in an injection-molding method. The conventional technology is more complicated in the structure and fabrication process. Further, the endoscope 10 has a larger size. Besides, the light-emitting surfaces of the light-emitting elements 11 are unlikely to face upwards, and the light-emitting elements 12 is hard to be disposed around the image sensor 11. Therefore, the conventional endoscope has disadvantages of low light utilization efficiency, non-uniform illumination, and likeliness of shadows and blind spots.

Accordingly, the manufacturers are eager to develop an endoscope that is miniaturized and able to provide uniform illumination.

SUMMARY OF THE INVENTION

The present invention proposes an image sensor package and an endoscope using the same, wherein the image sensor package includes a second substrate having an accommodating portion and the image sensor protrudes from the accommodating portion of the second substrate, and wherein the light-emitting elements disposed on the second substrate may be arranged near the image sensor, whereby to reduce the size of the image sensor package and provide better illumination.

In one embodiment, the image sensor package of the present invention comprises a first substrate, an image sensor, a second substrate, a light-emitting element, and a first encapsulant. The first substrate includes a plurality of first electric-conduction contacts, a plurality of second electric-conduction contacts, and a plurality of third electric-conduction contacts, wherein the plurality of second electric-conduction contacts and the plurality of third electric-conduction contacts are electrically connected with the plurality of corresponding first electric-conduction contacts. The image sensor is disposed on the first substrate and electrically connected with the plurality of second electric-conduction contacts. The second substrate is disposed on the first substrate and includes a plurality of fourth electric-conduction contacts, a plurality of fifth electric-conduction contacts, and an accommodating portion, wherein the plurality of fourth electric-conduction contacts is electrically connected with the plurality of corresponding third electric-conduction contacts; the image sensor protrudes from the second substrate via the accommodating portion. The light-emitting element is disposed on the second substrate and near the image sensor and electrically connected with the plurality of fifth electric-conduction contacts. The first encapsulant is filled into a space between the image sensor and the light-emitting element.

In one embodiment, the endoscope of the present invention comprises a tube, an image sensor package, a plurality of cables, and an electric connector. The tube includes a first opening and a second opening. The end of the first opening of the tube is extended to a cavity. The image sensor package is disposed at the end of the first opening of the tube to capture images of a cavity and generate corresponding electronic signals. The image sensor package of the present invention comprises a first substrate, an image sensor, a second substrate, a light-emitting element, and a first encapsulant. The first substrate includes a plurality of first electric-conduction contacts, a plurality of second electric-conduction contacts, and a plurality of third electric-conduction contacts, wherein the plurality of second electric-conduction contacts and the plurality of third electric-conduction contacts are electrically connected with the plurality of corresponding first electric-conduction contacts. The image sensor is disposed on the first substrate and electrically connected with the plurality of second electric-conduction contacts. The second substrate is disposed on the first substrate and includes a plurality of fourth electric-conduction contacts, a plurality of fifth electric-conduction contacts, and an accommodating portion, wherein the plurality of fourth electric-conduction contacts is electrically connected with the plurality of corresponding third electric-conduction contacts; the image sensor protrudes from the second substrate via the accommodating portion. The light-emitting element is disposed on the second substrate and near the image sensor and electrically connected with the plurality of fifth electric-conduction contacts. The first encapsulant is filled into a space between the image sensor and the light-emitting element. The plurality of cables is disposed inside the tube. One end of the plurality of cables is electrically connected with the plurality of corresponding first electric-conduction contacts. The electric connector is electrically connected with another end of the plurality of cables, whereby the endoscope can be electrically connected with an external electronic device in a pluggable way.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENTS

Various embodiments of the present invention will be described in detail below and illustrated in conjunction with the accompanying drawings. In addition to these detailed descriptions, the present invention can be widely implemented in other embodiments, and apparent alternations, modifications and equivalent changes of any mentioned embodiments are all included within the scope of the present invention and based on the scope of the Claims. In the descriptions of the specification, in order to make readers have a more complete understanding about the present invention, many specific details are provided; however, the present invention may be implemented without parts of or all the specific details. In addition, the well-known steps or elements are not described in detail, in order to avoid unnecessary limitations to the present invention. Same or similar elements in Figures will be indicated by same or similar reference numbers. It is noted that the Figures are schematic and may not represent the actual size or number of the elements. For clearness of the Figures, some details may not be fully depicted.

Figure 1:
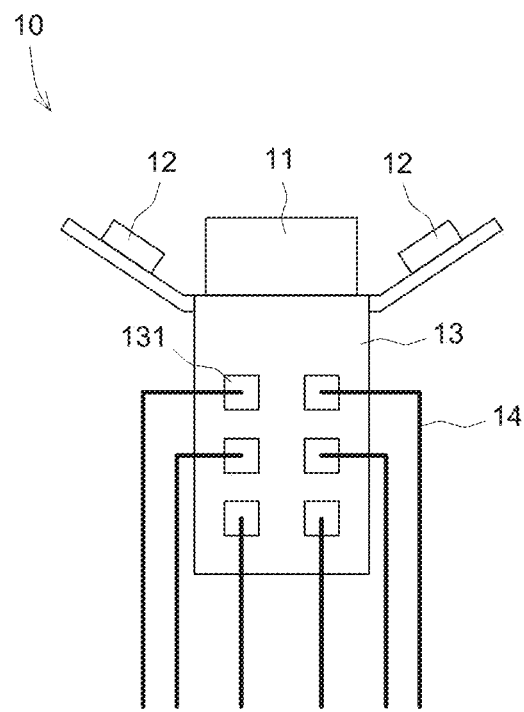
FIG. 1 is a diagram schematically showing a conventional image sensor module of an endoscope.
Figure 2:
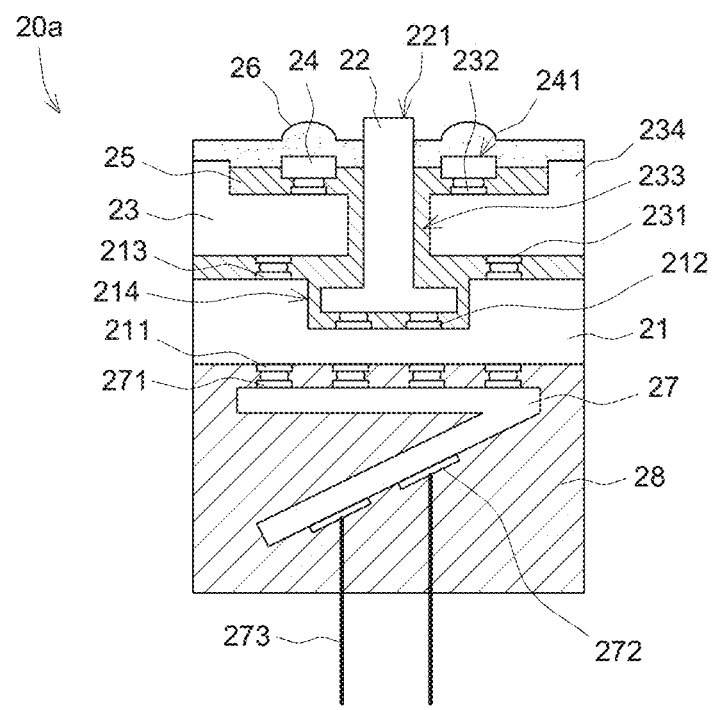
FIG. 2 is a diagram schematically showing an image sensor package according to a first embodiment of the present invention.

Refer to FIG. 2. The image sensor package 20a of the present invention comprises a first substrate 21, an image sensor 22, a second substrate 23, a light-emitting element 24, and a first encapsulant 25. The first substrate 21 includes a plurality of first electric-conduction contacts 211, a plurality of second electric-conduction contacts 212, and a plurality of third electric-conduction contacts 213, wherein the plurality of second electric-conduction contacts 212 and the plurality of third electric-conduction contacts 213 are electrically connected with the plurality of corresponding first electric-conduction contacts 211 through metal routes of the first substrate 21 or other appropriate electric-conduction paths. In one embodiment, the plurality of second electric-conduction contacts 212 and the plurality of third electric-conduction contacts 213 are disposed on one side opposite to the plurality of first electric-conduction contacts 211. In one embodiment, the first substrate 21 is a ceramic substrate. The image sensor 22 is disposed on the first substrate 21 and electrically connected with the corresponding second electric-conduction contacts 212.

The second substrate 23 is disposed on the first substrate 21 and includes a plurality of fourth electric-conduction contacts 231, a plurality of fifth electric-conduction contacts 232, and a through-hole 233. In one embodiment, the plurality of fourth electric-conduction contacts 231 and the plurality of fifth electric-conduction contacts 232 are respectively disposed on two opposite sides of the second substrate 23. It is easily understood: the plurality of fourth electric-conduction contacts 231 may be electrically connected with the plurality of corresponding fifth electric-conduction contacts 232 on the opposite side through metal routes of the second substrate 23 or other appropriate electric-conduction paths. The plurality of fourth electric-conduction contacts 231 of the second substrate 23 is electrically connected with the plurality of corresponding third electric-conduction contacts 213 of the first substrate 21. For example, a tin paste, a silver glue, or another appropriate method may join the plurality of fourth electric-conduction contacts 231 of the second substrate 23 to the plurality of corresponding third electric-conduction contacts 213 of the first substrate 21 and function as electric-conduction paths. The image sensor 22 passes through the through-hole 233 of the second substrate 23 and protrudes from the second substrate 23. The light-emitting element 24 is disposed on the second substrate 23 and electrically connected with the plurality of corresponding fifth electric-conduction contacts 232 of the second substrate 23. The light-emitting element 24 may be electrically connected with an external device through the fifth electric-conduction contacts 232 and the fourth electric-conduction contacts 231 of the second substrate 23 and the third electric-conduction contacts 213 and the first electric-conduction contacts 211 of the first substrate 21 in sequence. In one embodiment, the image sensor package 20a comprises a plurality of light-emitting elements 24. The plurality of light-emitting elements 24 may respectively emit light beams having different wavelengths. The plurality of light-emitting elements 24 may be simultaneously or separately operated for different purposes or objects. It is easily understood: the plurality of light-emitting elements 24 may emit light beams having the same wavelength for illumination or other specific purposes. For example, the light-emitting elements 24 may be white light-emitting diodes (LED), infrared LEDs, blue LEDs, ultraviolet LEDs, or a combination thereof.

Figure 3:
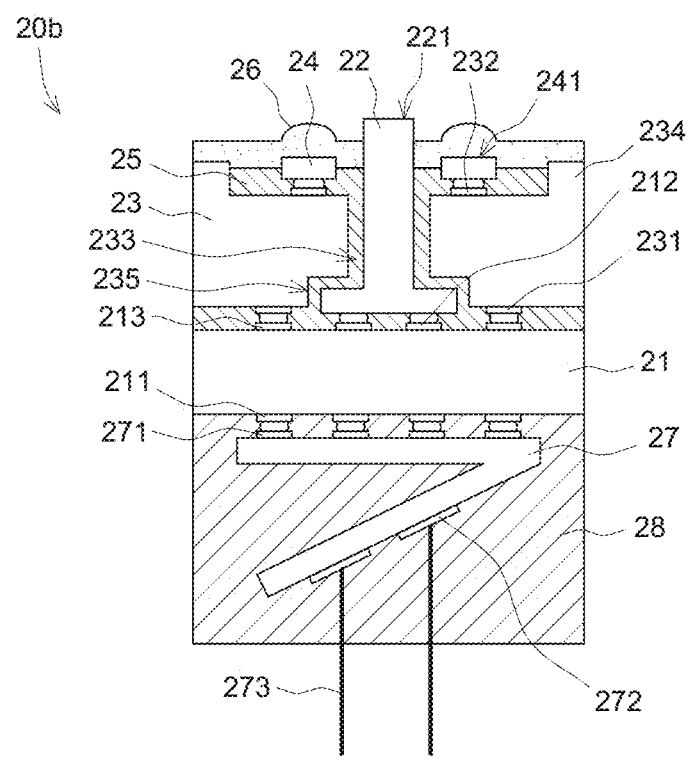
FIG. 3 is a diagram schematically showing an image sensor package according to a second embodiment of the present invention.

The first encapsulant 25 is filled into a space between the image sensor 22 and the light-emitting element 24 to fix and protect the image sensor 22 and the light-emitting element 24. According to the design of the fabrication process, the first encapsulant 25 may be filled into the gaps between the first substrate 21 and the second substrate 23 via the through-hole 233 to enhance the joint strength of the first substrate 21 and the second substrate 23, as shown in FIG. 3. It is easily understood: the first encapsulant 25 may be merely formed on the second substrate 23. In one embodiment, the first encapsulant 25 is made of a semi-transparent or opaque resin, whereby to prevent the imaging system of the image sensor 22 from being influenced by the illumination light or stray light, which is emitted by the light-emitting element 24. For example, the semi-transparent resin may have a transmittance of 0.01 to 50%. It is easily understood: the light-emitting surface 241 of the light-emitting element 24 must be higher than or equal to the top surface of the first encapsulant 25 to avoid the shielding of the light output from the light-emitting element 24. In other words, the first encapsulant 25 cannot cover the light-emitting surface 241 of the light-emitting element 24. In one embodiment, the second substrate 23 includes a dam 234, which is disposed around the light emitting element 24. The dam 234 can limit the area where the first encapsulant 25 is filled. In one embodiment, the height of the dam 234 is equal to or lower than the height of the light-emitting surface 241 of the light-emitting element 24 lest the first encapsulant 25 cover the light-emitting surface 241 of the light-emitting element 24.

In one embodiment, the image sensor package 20a further comprises a secondary optical structure 26. The secondary optical structure 26 is disposed on the light-emitting side of the light-emitting element 24. The secondary optical structure 26 can adjust the light-exiting angle so as to increase the utilization rate of illumination and the distance of illumination. It can be understood that the secondary optical structure 26 can be disposed on the light-emitting surface 241 of the light-emitting element 24.

In one embodiment, the image sensor package 20a further comprises a circuit board 27 and a plurality of cables 273. The circuit board 27 includes a plurality of sixth electric-conduction contacts 271 and a plurality of seventh electric-conduction contacts 272, wherein the plurality of sixth electric-conduction contacts 271 of the circuit board 27 is electrically connected with the plurality of first electric-conduction contacts 211 of the first substrate 21. In one embodiment, the circuit board 27 may be a printed circuit board (PCB) or a flexible printed circuit (FPC). The plurality of cables 273 is electrically connected with the plurality of corresponding seventh electric-conduction contacts 272. The plurality of cables 273 may function as power cables and signal transmission cables, whereby the image sensor package 20a may be electrically connected with the exterior. For an example, the image sensor package 22 may be connected with a power supply or transmit image signals to a rear-end controller or a display device. In one embodiment, the image sensor package 20a further comprises a second encapsulant 28. The second encapsulant 28 covers the circuit board 27 and one end of the plurality of cables 273 lest the cables 273 be separated from the circuit board 27.

It is easily understood: the relative height of the image sensor 22 and the light-emitting element 24 may influence the illumination and the imaging quality. For example, if the light-emitting surface 241 of the light-emitting element 24 is relatively too low with respect to the image sensor 22, the image sensor 22 may block the illuminating light emitted by the light-emitting element 24 and generate shadows; if the light incident surface 221 of the image sensor 22 is relatively too low with respect to the light-emitting element 24, the light-emitting element 24 may block the imaging light reflected by the inspected object; alternatively, the illuminating light emitted by the light-emitting element 24 may directly enter the image sensor 22 and affect the imaging quality. According to the structure shown in FIG. 2, merely adjusting the thickness of the second substrate 23 is sufficient to control the relative height of the light incident surface 221 of the image sensor 22 and the light-emitting surface 241 of the light-emitting element 24 and optimize the illumination and the imaging quality. In one embodiment, the height of the light incident surface 221 of the image sensor 22 is higher than or equal to the height of the light-emitting surface 241 of the light-emitting element 24. It is preferred: the height difference of the light incident surface 221 of the image sensor 22 and the light-emitting surface 241 of the light-emitting element 24 is smaller than or equal to 0.5 mm.

It should be explained herein: the higher the resolution of the image sensor, the more the electric-conduction contacts required; thus the electric-connection end of the image sensor 22 (the end facing the first electric-conduction contacts 211) needs a larger area. As shown in FIG. 2, the section area of the electric-connection end of the image sensor 22 is greater than the area of the light incident surface 221 of the image sensor 22. Thus, the image sensor 22 has an inverse-T structure. In other words, the electric-connection end of the image sensor 22 extends laterally to form a protrudent portion. The inverse-T image sensor 22 would hinder the light-emitting elements 24 from being disposed near the image sensor 22, increase the size of the image sensor package, and reduce the illumination effect.

Refer to FIG. 2. In one embodiment, the first substrate 21 further includes a cavity 214 to overcome the abovementioned problem. The plurality of second electric-conduction contacts 212 and the image sensor 22 are disposed on the bottom of the cavity 214. In the case that the height of the lateral protrudent portion of the image sensor 22 is equal to or smaller than the depth of the cavity 214 of the first substrate 21, the second substrate 23 may extend toward the image sensor 22. Briefly to speak, the inner diameter of the through-hole 233 of the second substrate 23 is smaller than the maximum inner diameter of the cavity 214 of the first substrate 21, and a portion of the second substrate 23 covers the cavity 214 of the first substrate 21, that is a portion of the second substrate 23 is projected on the bottom of the cavity 214. Based on the abovementioned structure, the light-emitting elements 24 may be disposed on the second substrate 23 and be closed to the image sensor 22 to reduce the size of the image sensor package 20a and significantly promote the illumination effect. It is easily understood: the cavity formed in the second substrate can also achieve the abovementioned objective. Refer to FIG. 3 for an image sensor package 20b. In the image sensor package 20b, the second substrate 23 further includes a cavity 235, and the through-hole 233 passes through the bottom of the cavity 235. Based on the abovementioned structure, the image sensor 22 may protrude from the second substrate 23 via the through-hole 233, and the lateral protrudent portion of the image sensor 22 may be accommodated by the cavity 235 of the second substrate 23, that is a portion of the lateral protrudent portion of the image sensor 22 is projected on the bottom of the cavity 235.

In the above embodiment, the second substrate 23 uses the through-hole 233 as the accommodating portion to accommodate the image sensor 22, so that the second substrate 23 surrounds the image sensor 22, but it is not limited. In one embodiment, referring to FIG. 9, the second substrate 23 can use a notch as the accommodating portion, so that the second substrate 23 may be arranged around the image sensor 22 in a U-shape or an L-shape. According to this structure, the space on the side of the image sensor 22 where the second substrate 23 is not provided can be further omitted to further reduce the volume of the image sensor package 20e.

Figure 9:
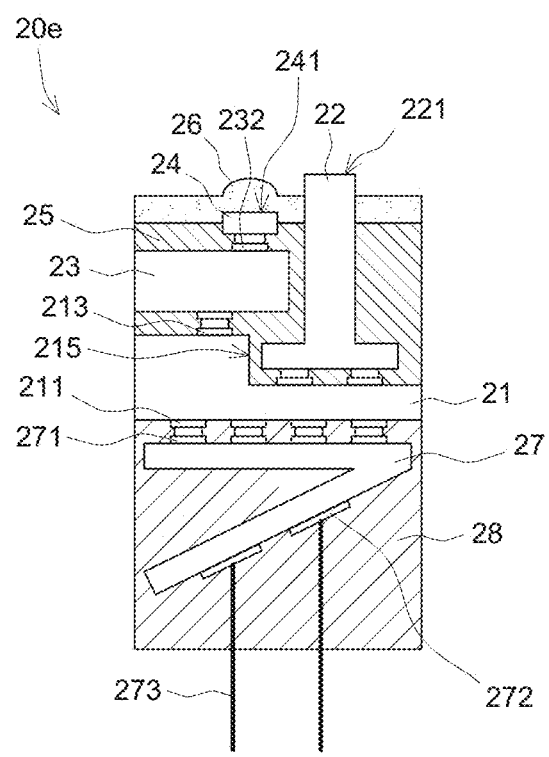
FIG. 9 is a diagram schematically showing an image sensor package according to a fifth embodiment of the present invention.

It can be understood that one of the side walls of the cavity 214 of the first substrate 21 shown in FIG. 2 can be omitted to form the step structure 215 shown in FIG. 9. The arrangement position of the image sensor 22, the relative positions of the second substrate 23, the lateral protrudent portion of the image sensor 22 and the step structure 215 of the first substrate 21 are described in the embodiment shown in FIG. 2 and will not be repeated here. According to the embodiment shown in FIG. 9, the height of the lateral protrudent portion of the image sensor 22 is less than or equal to the height of the step structure, and a protrusion of the second substrate 23 is projected on the bottom of the step structure 215, so that the light emitting element 24 is closer to image sensor 22. Similarly, one of the side walls of the cavity 235 of the second substrate 23 shown in FIG. 3 can be omitted, and then a step structure is formed on the second substrate 23. According to this structure, the lateral protrudent portion of the image sensor 22 can be accommodated in the step structure of the second substrate 23, so that a portion of the second substrate 23 is projected on the lateral protrudent portion of the image sensor.

Figure 4:
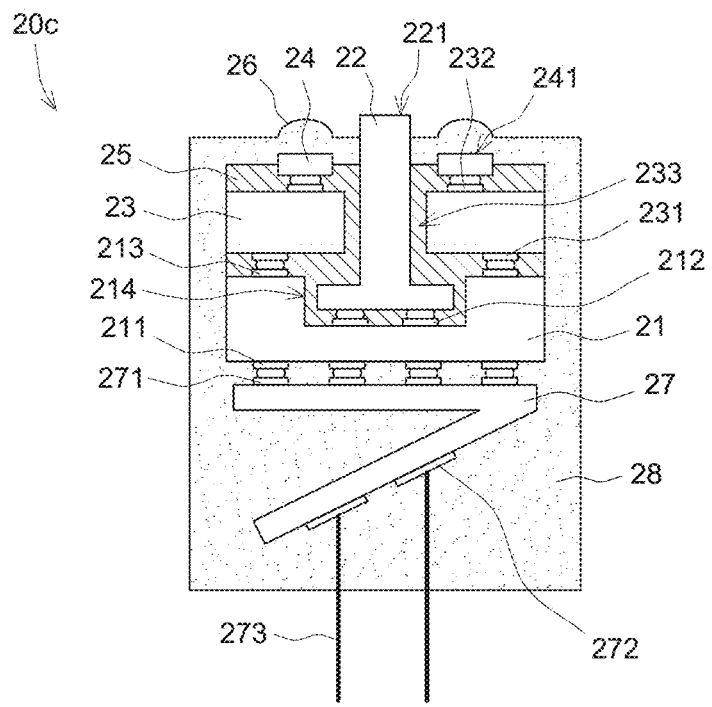
FIG. 4 is a diagram schematically showing an image sensor package according to a third embodiment of the present invention.

In the embodiments shown in FIG. 2 and FIG. 3, the secondary optical structure 26 and the second encapsulant 28 are formed separately. However, the present invention is not limited by these embodiments. Refer to FIG. 4. In one embodiment, the secondary optical structure 26 of the image sensor package 20c and the second encapsulant 28 are formed simultaneously. In one embodiment, the mold where the second encapsulant 28 is filled includes the structure corresponding to the secondary optical structure 26. After the second encapsulant 28 is filled, the second encapsulant 28 not only encapsulates the circuit board 27 and one end of the plurality of cables 273 but also covers the light-emitting element 24. After demolding, the secondary optical structure 26 is formed in the light-emitting side of the light-emitting element 24. It should be further explained herein: each of the image sensor packages shown in FIG. 2 and FIG. 3 includes the dam 234; however, the present invention is not limited by these embodiments. After the first encapsulant 25 has been filled, the dam 234 may be removed during the cutting process so as to reduce the size of the image sensor package, such as the image sensor package 20c shown in FIG. 4.

Figure 5:
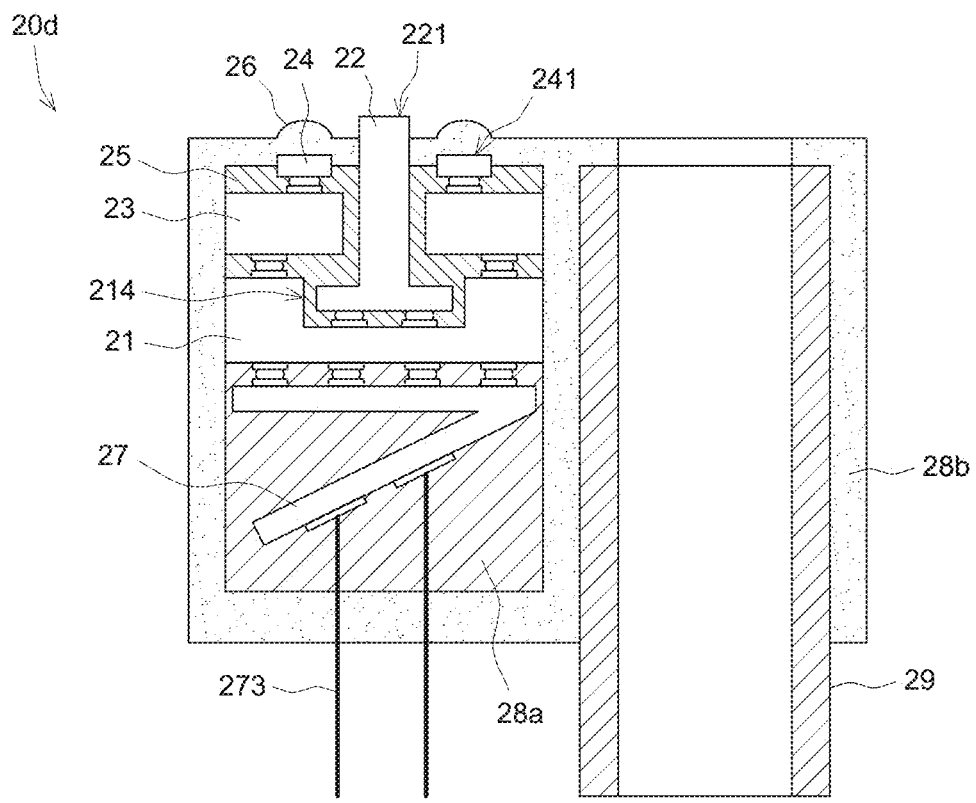
FIG. 5 is a diagram schematically showing an image sensor package according to a fourth embodiment of the present invention.

Refer to FIG. 5. In one embodiment, the image sensor package 20d further comprises a pipe 29. The pipe 29 is disposed beside the first substrate 21 along the sensing direction of the image sensor 22. The second encapsulant 28b encapsulates one end of the pipe 29 and keeps the opening of the pipe 29 unlocked. The pipe 29 may join with a working channel, whereby to inject/suck liquid or transfer an instrument to a target position during the operation of the endoscope. It should be explained: the second encapsulant may be formed in several stages. In the embodiment shown in FIG. 5, a second encapsulant 28a is used to encapsulate the circuit board 27 and the cables 273 beforehand, and then a second encapsulant 28b is used to encapsulate the pipe 29 and form the secondary optical structure 26 on the light-emitting side of the light-emitting element 24.

Figure 6A:
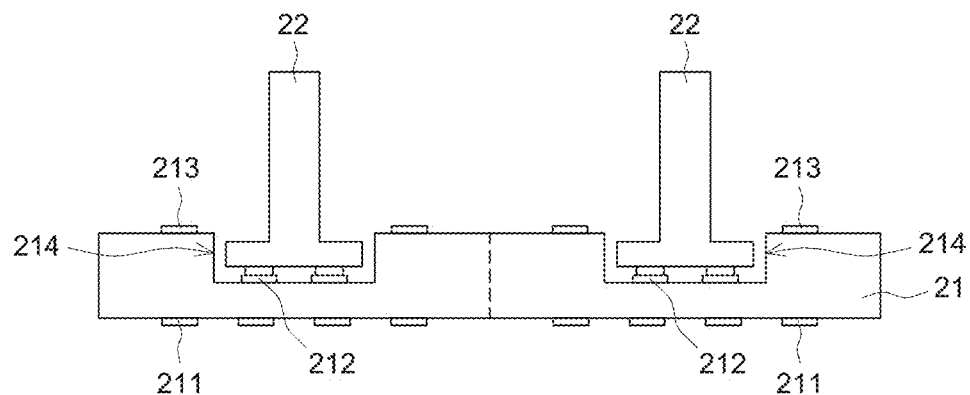
FIGS. 6a-6e are diagrams schematically showing a method for fabricating an image sensor package according to one embodiment of the present invention.

Refer to FIGS. 6a-6e for a method of fabricating the image sensor package 20d shown in FIG. 5. Refer to FIG. 6a. Firstly, provide a substrate 21, which includes a plurality of cavities 214 arranged in array, a plurality of first electric-conduction contacts 211, a plurality of second electric-conduction contacts 212, and a plurality of third electric-conduction contacts 213, wherein the first electric-conduction contacts 211, the second electric-conduction contacts 212 and the third electric-conduction contacts 213 are corresponding to the cavities 214, and wherein the plurality of second electric-conduction contacts 212 and the plurality of third electric-conduction contacts 213 are electrically connected with the plurality of corresponding first electric-conduction contacts 211 through metal wires of the first substrates 21 or other appropriate electric-conduction paths. The image sensors 22 are respectively disposed in the cavities 214 by a die-bonding method and electrically connected with the second electric-conduction contacts 212 inside the cavities 214.

Figure 6B:
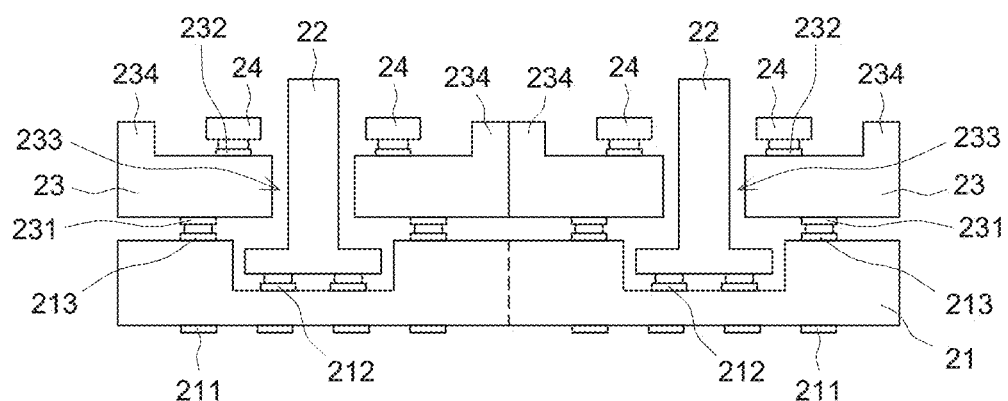

Refer to FIG. 6b. Next, align the through-holes 233 of the second substrates 23 to the image sensors 22, and make the through-holes 233 sleeve the image sensors 22; dispose and bond the second substrates 23 onto the first substrates 21; electrically connect the plurality of fourth electric-conduction contacts 231 of the second substrates 23 with the plurality of corresponding third electric-conduction contacts 213 of the first substrates 21. In one embodiment, the second substrates 23 may be bonded to and electrically connected with the first substrates 31 in a eutectic bonding method or a solder joint method. However, the present invention is not limited by the embodiment. In one embodiment, the plurality of fourth electric-conduction contacts 231 of the second substrate 23 is electrically connected with the plurality of corresponding third electric-conduction contacts 213 of the first substrate 21 to form electric-conduction paths using a tin paste, a silver glue, or another appropriate method. In one embodiment, the second substrates 23 are independent elements and respectively installed in the first substrates 21. In one embodiment, the second substrates 23 are jointly formed in a substrate, and the substrate includes a plurality of trough-holes 233 arranged in array, a plurality of fourth electric-conduction contacts 231 and a plurality of fifth electric-conduction contacts 232, wherein the plurality of fourth electric-conduction contacts 231 and the plurality of fifth electric-conduction contacts 232 are corresponding to the through-holes 233. The plurality of fourth electric-conduction contacts 231 may be electrically connected with the plurality of fifth electric-conduction contacts 232, which is corresponding to the plurality of fourth electric-conduction contacts 231 and on the opposite side of the plurality of fourth electric-conduction contacts 231, through metal routes of the second substrates 23 or other appropriate electric-conduction paths. Next, dispose the light-emitting elements 24 on the second substrates 23, and electrically connect the light-emitting elements 23 with the plurality of corresponding fifth electric-conduction contacts 232 of the second substrates 23.

Figure 6C:
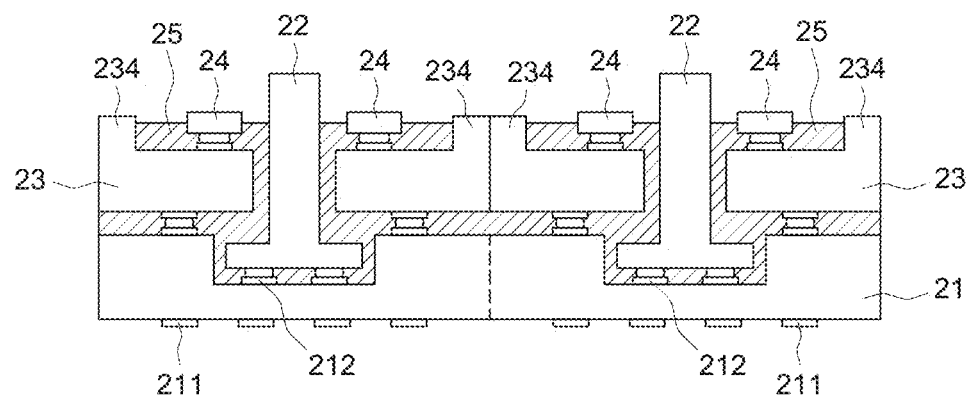

Refer to FIG. 6c. Next, fill the first encapsulant 25 into the gaps between the image sensors 22 and the light-emitting elements 24, and cure the first encapsulant 25 by an ultraviolet method, a thermal method or another appropriate method. In the embodiment shown in FIG. 6c, the second substrate 23 includes a surrounding dam 234, which is used to limit the area where the first encapsulant 25 is filled. According to the design of the fabrication process, the first encapsulant 25 may be filled into the gaps between the first substrate 21 and the second substrate 23 via the through-hole 233 to enhance the joint strength of the first substrate 21 and the second substrate 23, as shown in FIG. 6c. It is easily understood: the first encapsulant 25 may be merely formed on the second substrate 23.

Figure 6D:
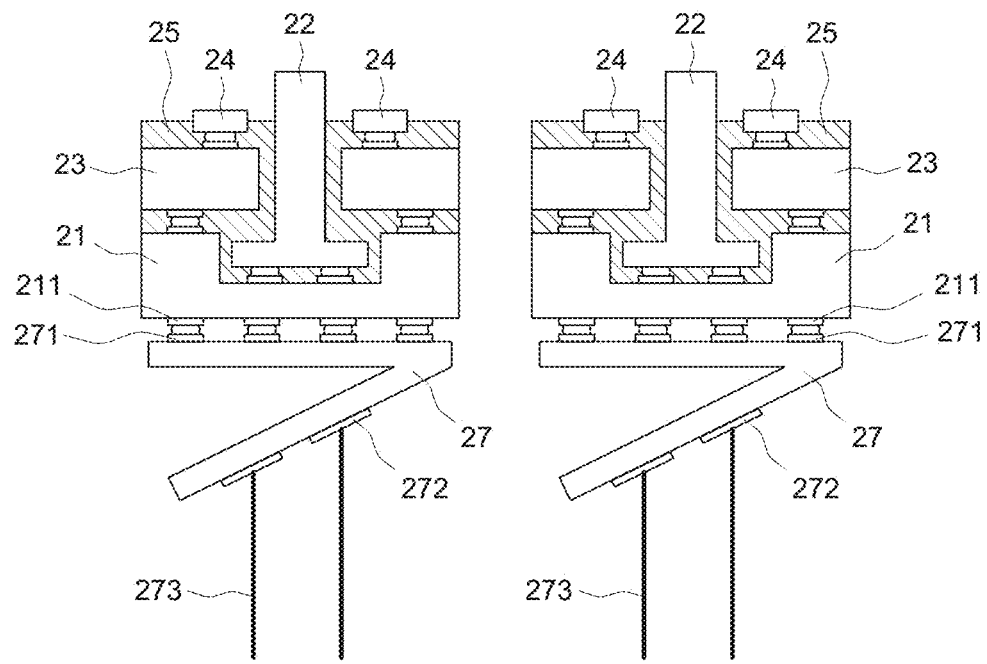

Next, cut the substrate 21 along the cutting alignment marks or the cutting lines (such as the dashed line shown in FIG. 6c) to generate image sensor modules each including the image sensor 22 and the light-emitting elements 24. Refer to FIG. 6d. During the cutting process, the dam 234 may be removed so as to reduce the size of the image sensor module. Next, dispose the separate image sensor module on the circuit board 27 in a surface mount technology (SMT) or another appropriate technology, and electrically connect the image sensor module with the circuit board 27. Next, electrically connect the plurality of cables 273 with the corresponding seventh electric-conduction contacts 272 of the circuit board 27.

Figure 6E:
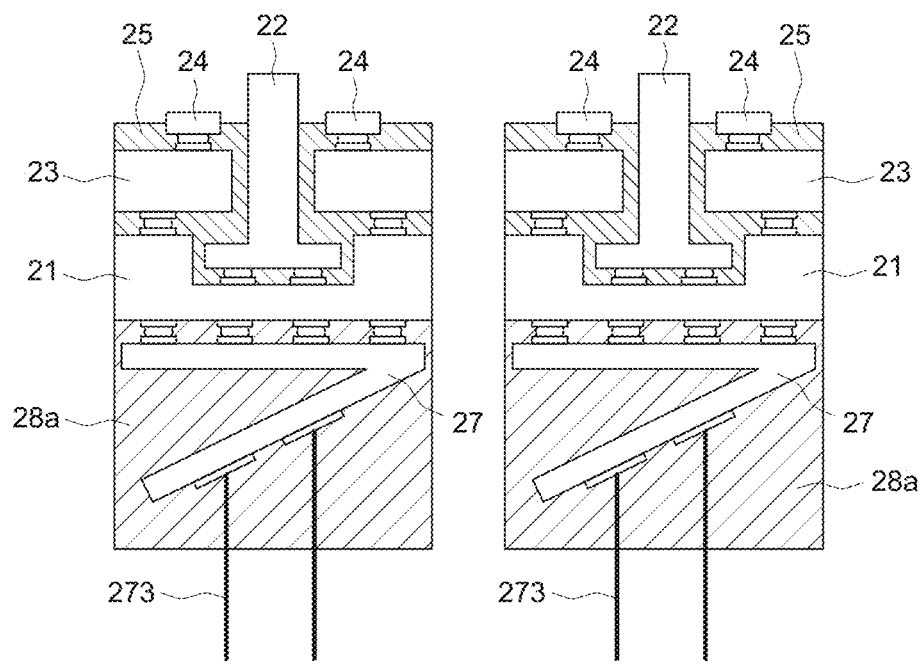

Refer to FIG. 6e. Next, fill the second encapsulant 28a into the mold to make the second encapsulant 28a encapsulate the circuit board 27 and one end of the cables 273 lest external force detach the circuit board 27 or the cables 273. Then, arrange the pipe 29 beside the image sensor module shown in FIG. 6e, and use the second encapsulant 28b to encapsulate one end of the pipe 20 with the openings of the pipe 20 unlocked. Thus is completed the image sensor package 20d shown in FIG. 5.

Figure 7:
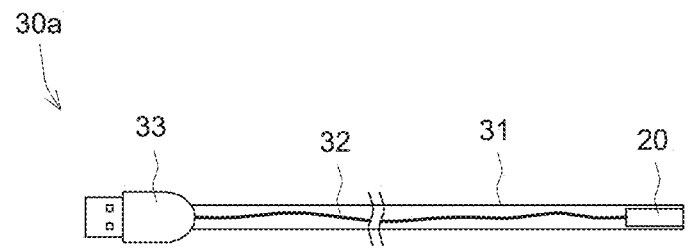
FIG. 7 is a diagram schematically showing an endoscope according to one embodiment of the present invention.

Refer to FIG. 7. In one embodiment, the endoscope 30a of the present invention comprises a tube 31, an image sensor package 20, a plurality of cables 32, and an electric connector 33. The tube 31 includes a first opening and a second opening. The end of the first opening of the tube 31 of the endoscope 30a is extended to a cavity, such as a cavity of a human body or a small space to be inspected in an industrial inspection. It is easily understood: the tube 31 may be designed to have different appearances to meet different applications. The image sensor package 20 is disposed at the first opening of the tube 31, whereby to capture images of a cavity and generate corresponding electronic signals. The detailed structure of the image sensor package 20 has been described hereinbefore and will not repeat again.

The cables 32 are respectively electrically connected with the image sensor package 20 and the electric connector 33, whereby the electronic signals generated by the image sensor package 20 may be transmitted to an external electronic device, such as a computer, a mobile Internet-access device or a dedicated electronic device of the endoscope, through the electric connector 33. In one embodiment, the electric connector 33 is electrically connected with an external electronic device in a pluggable way. The electric connector 33 may be a USB interface, a connection interface of a mobile Internet-access device or another appropriate electric connector.

Figure 8:
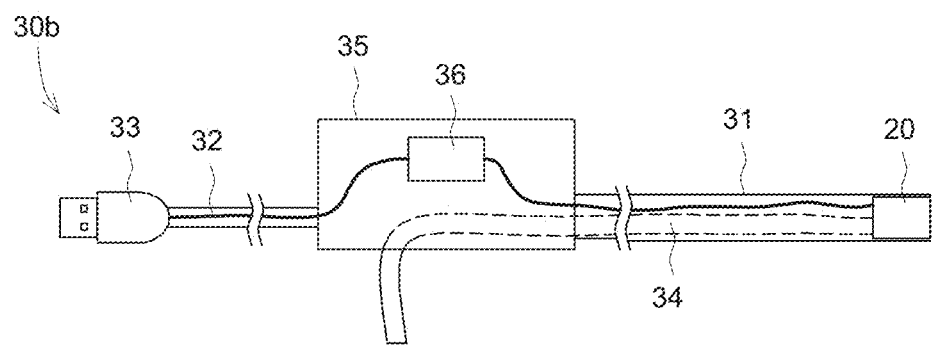
FIG. 8 is a diagram schematically showing an endoscope according to another embodiment of the present invention.

Refer to FIG. 8. In one embodiment, the tube 31 of the endoscope 30b of the present invention further includes a working channel 34. The operator may extend a working instrument through the working channel 34 into a cavity to undertake an intended work, such as sampling tissue, sucking out secretions/tissue fluids/blood, or supplying medicine.

In one embodiment, the endoscope 30b of the present invention further comprises a housing 35. The housing 35 is disposed between the tube 31 and the electric connector 33. The design of the housing 33 may be varied according to requirement. For an example, the housing 35 may have an appearance suitable to be held by the operator. For another example, the shape of the housing 35 is suitable to be mounted on a carrier, such as a head-mounted carrier. In one embodiment, the endoscope 30b of the present invention further comprises an electronic element 36. The electronic element 36 is electrically connected with the image sensor package 20 and the electric connector 33. The electronic element 36 can process the electronic signals generated by the image sensor package 20 and transmit the electronic signals to an external electronic device through the electric connector 33. In one embodiment, the electronic element 36 is a microcontroller unit (MCU).

In conclusion, the present invention proposes an image sensor package and an endoscope using the same, wherein the image sensor package comprises a second substrate having a through-hole or a notch; the image sensor protrudes from the second substrate via the through-hole or a notch; the light-emitting elements disposed on the second substrate, whereby the relative height of the image sensor and the light-emitting elements may be optimized via adjusting the thickness of the second substrate. Besides, the second substrate can be extended toward the image sensor, whereby the light-emitting elements may be disposed near the image sensor. Therefore, the present invention can reduce the size of the image sensor package and provide better illumination.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the appended claims.

What is claimed is:

1. An image sensor package, comprising:
a first substrate, including a plurality of first electric-conduction contacts, a plurality of second electric-conduction contacts, and a plurality of third electric-conduction contacts, wherein the plurality of second electric-conduction contacts and the plurality of third electric-conduction contacts are electrically connected with the plurality of corresponding first electric-conduction contacts;
an image sensor, disposed on the first substrate and electrically connected with the plurality of second electric-conduction contacts;
a second substrate, disposed on the first substrate and includes a plurality of fourth electric-conduction contacts, a plurality of fifth electric-conduction contacts, and an accommodating portion, wherein the plurality of fourth electric-conduction contacts is electrically connected with the plurality of corresponding third electric-conduction contacts, and the image sensor protrudes from the second substrate via the accommodating portion;
a light-emitting element, disposed on the second substrate and near the image sensor and electrically connected with the plurality of fifth electric-conduction contacts; and
a first encapsulant, filled into a space between the image sensor and the light-emitting element.

2. The image sensor package according to claim 1, wherein the accommodating portion of the second substrate is a through-hole or a notch.

3. The image sensor package according to claim 2, wherein the first substrate further includes a cavity or a step structure, the plurality of second electric-conduction contacts and the image sensor are disposed on a bottom of the cavity or the step structure, and a portion of the second substrate is projected on the bottom of the cavity or the step structure.

4. The image sensor package according to claim 3, wherein the image sensor includes a protrudent portion extending laterally, and a height of the protrudent portion is equal to or smaller than a depth of the cavity or a height of the step structure.

5. The image sensor package according to claim 2, wherein the second substrate further includes a cavity, and the through-hole penetrates a bottom of the cavity.

6. The image sensor package according to claim 1, wherein the image sensor includes a protrudent portion extending laterally, and an inner wall of the accommodating portion of the second substrate includes a step structure so that a portion of the second substrate is projected on the protrudent portion of the image sensor.

7. The image sensor package according to claim 1, wherein the image sensor includes a light incident surface and an electric-connection end, and a section area of the electric-connection end is larger than an area of the light incident surface.

8. The image sensor package according to claim 1, wherein a height of a light incident surface of the image sensor is equal to or higher than a height of a light-emitting surface of the light-emitting element.

9. The image sensor package according to claim 1, wherein a height of a light incident surface of the image sensor is higher than a height of a light-emitting surface of the light-emitting element, and a height difference between the light incident surface of the image sensor and the light-emitting surface of the light-emitting element is equal to or smaller than 0.5 mm.

10. The image sensor package according to claim 1, comprising a plurality of light-emitting elements; and the plurality of light-emitting elements emit light beams respectively having different wavelengths or emits light beams having an identical wavelength.

11. The image sensor package according to claim 1, wherein the second substrate further includes a dam, which is disposed around the light emitting element to form an area where the first encapsulant is filled.

12. The image sensor package according to claim 11, wherein a height of the dam is equal to or smaller than a height of a light-emitting surface of the light-emitting element.

13. The image sensor package according to claim 1, wherein the first encapsulant is made of a semi-transparent resin or an opaque resin.

14. The image sensor package according to claim 1, further comprising
a secondary optical structure, disposed on a light-emitting side of the light-emitting element.

15. The image sensor package according to claim 1, further comprising
a circuit board, including a plurality of sixth electric-conduction contacts and a plurality of seventh electric-conduction contacts, wherein the plurality of sixth electric-conduction contacts is electrically connected with the plurality of corresponding first electric-conduction contacts of the first substrate; and
a plurality of cables, electrically connected with the plurality of corresponding seventh electric-conduction contacts.

16. The image sensor package according to claim 15, further comprising
a second encapsulant, encapsulating the circuit board and one end of the plurality of cables.

17. The image sensor package according to claim 15, further comprising
a second encapsulant, encapsulating the light-emitting element, the circuit board and one end of the plurality of cables and including a secondary optical structure corresponding to the light-emitting element.

18. The image sensor package according to claim 15, further comprising
a pipe, disposed beside the first substrate along a sensing direction of the image sensor; and
a second encapsulant, encapsulating the light-emitting element, the circuit board, one end of the plurality of cables, and one end of the pipe.

19. The image sensor package according to claim 18, wherein the second encapsulant includes a secondary optical structure corresponding to the light-emitting element.

20. An endoscope, comprising:
a tube, including a first opening and a second opening, wherein an end of the first opening of the tube is to be extended to a cavity;
an image sensor package, disposed at the end of the first opening of the tube to capture images of the cavity and generate corresponding electronic signals, and including
a first substrate, including a plurality of first electric-conduction contacts, a plurality of second electric-conduction contacts, and a plurality of third electric-conduction contacts, wherein the plurality of second electric-conduction contacts and the plurality of third electric-conduction contacts are electrically connected with the plurality of corresponding first electric-conduction contacts;
an image sensor, disposed on the first substrate and electrically connected with the plurality of second electric-conduction contacts;
a second substrate, disposed on the first substrate and includes a plurality of fourth electric-conduction contacts, a plurality of fifth electric-conduction contacts, and an accommodating portion, wherein the plurality of fourth electric-conduction contacts is electrically connected with the plurality of corresponding third electric-conduction contacts, and the image sensor protrudes from the second substrate via the accommodating portion;
a light-emitting element, disposed on the second substrate and near the image sensor and electrically connected with the plurality of fifth electric-conduction contacts; and
a first encapsulant, filled into a space between the image sensor and the light-emitting element;
a plurality of cables, disposed inside the tube, wherein one end of the plurality of cables is electrically connected with the plurality of corresponding first electric-conduction contacts of the first substrate; and
an electric connector, electrically connected with another end of the plurality of cables to enable the endoscope to be electrically connected with an external electronic device in a pluggable way.

21. The endoscope according to claim 20, further comprising:
an electronic element, electrically connected with the image sensor package and the electric connector and processing electronic signals generated by the image sensor package.

22. The endoscope according to claim 20, further comprising:
a housing, disposed between the image sensor package and the electric connector.

23. The endoscope according to claim 20, wherein the accommodating portion of the second substrate is a through-hole or a notch.

24. The endoscope according to claim 23, wherein the first substrate further includes a cavity or a step structure, the plurality of second electric-conduction contacts and the image sensor are disposed on a bottom of the cavity or the step structure, and a portion of the second substrate is projected on the bottom of the cavity or the step structure.

25. The endoscope according to claim 24, wherein the image sensor includes a protrudent portion extending laterally, and a height of the protrudent portion is equal to or smaller than a depth of the cavity or a height of the step structure.

26. The endoscope according to claim 23, wherein the second substrate further includes a cavity, and the through-hole penetrates a bottom of the cavity.

27. The endoscope according to claim 20, wherein the image sensor includes a protrudent portion extending laterally, and an inner wall of the accommodating portion of the second substrate includes a step structure so that a portion of the second substrate is projected on the protrudent portion of the image sensor.

28. The endoscope according to claim 20, wherein the image sensor includes a light incident surface and an electric-connection end, and a section area of the electric-connection end is larger than an area of the light incident surface.

29. The endoscope according to claim 20, wherein a height of a light incident surface of the image sensor is equal to or higher than a height of a light-emitting surface of the light-emitting element.

30. The endoscope according to claim 20, wherein a height of a light incident surface of the image sensor is higher than a height of a light-emitting surface of the light-emitting element, and a height difference between the light incident surface of the image sensor and the light-emitting surface of the light-emitting element is equal to or smaller than 0.5 mm.

31. The endoscope according to claim 20, wherein the image sensor package comprises a plurality of light-emitting elements, and the plurality of light-emitting elements emits light beams respectively having different wavelengths or emits light beams having an identical wavelength.

32. The endoscope according to claim 20, wherein the second substrate further includes a dam, which is disposed around the light emitting element to limit an area where the first encapsulant is filled.

33. The endoscope according to claim 20, wherein the first encapsulant is made of a semi-transparent resin or an opaque resin.

34. The endoscope according to claim 20, wherein the image sensor package further comprises:
 a secondary optical structure, disposed on a light-emitting side of the light-emitting element.

35. The endoscope according to claim 20, wherein the image sensor package further comprises:
 a circuit board, including a plurality of sixth electric-conduction contacts and a plurality of seventh electric-conduction contacts, wherein the plurality of sixth electric-conduction contacts is electrically connected with the plurality of corresponding first electric-conduction contacts of the first substrate, and the plurality of cables is electrically connected with the plurality of corresponding seventh electric-conduction contacts.

36. The endoscope according to claim 35, wherein the image sensor package further comprises:
 a second encapsulant, encapsulating the circuit board and one end of the plurality of cables.

37. The endoscope according to claim 35, wherein the image sensor package further comprises:
 a second encapsulant, encapsulating the light-emitting element, the circuit board and one end of the plurality of cables and including a secondary optical structure corresponding to the light-emitting element.

38. The endoscope according to claim 35, wherein the image sensor package further comprises:
 a pipe, disposed beside the first substrate along a sensing direction of the image sensor; and
 a second encapsulant, encapsulating the light-emitting element, the circuit board, one end of the plurality of cables, and one end of the pipe.

39. The endoscope according to claim 38, wherein the second encapsulant includes a secondary optical structure corresponding to the light-emitting element.

40. The endoscope according to claim 38, wherein the tube includes a working channel; one end of the working channel is joined with the pipe of the image sensor package.

* * * * *